United States Patent [19]
Kung et al.

[11] Patent Number: 5,180,378
[45] Date of Patent: Jan. 19, 1993

[54] LASER SURGERY SYSTEM

[75] Inventors: Robert T. V. Kung, Andover; Robert B. Stewart, Haverhill, both of Mass.

[73] Assignee: Abiomed, Inc., Danivers, Mass.

[21] Appl. No.: 613,110

[22] Filed: Nov. 14, 1990

Related U.S. Application Data

[63] Continuation of Ser. No. 342,481, Apr. 24, 1989, abandoned.

[51] Int. Cl.⁵ .............................. A61N 5/02
[52] U.S. Cl. .......................... 606/10; 606/2; 606/3; 606/16; 372/3; 372/25; 372/29; 372/59; 372/72
[58] Field of Search ...................... 372/3, 9, 25, 29, 51, 372/53, 54, 55, 59, 72; 307/426; 128/395, 397, 398; 606/2-18

[56] References Cited

U.S. PATENT DOCUMENTS

| | | |
|---|---|---|
| 4,144,464 | 3/1979 | Loree et al. |
| 4,178,565 | 12/1979 | Morton et al. ........................ 372/3 |
| 4,327,337 | 4/1982 | Liu ........................................ 372/3 |

FOREIGN PATENT DOCUMENTS 8706478 11/1987 World Int. Prop. O. .............. 606/9

OTHER PUBLICATIONS

"A Universal Fiber Optic (UFO) Measurement System Based on Near 1R Fiber Raman Lasers" by Cohen et al; IEEE J of Quantum Electron; vol. QE-14 No. 11; Nov. 1978 pp. 855-859.

"Phase Front Reproduction in Raman Conversion" by Kung et al; IEEE J of Quantum Electron. vol. QE-No. 8; Aug. 1982 pp. 1306-1310.

*Primary Examiner*—David M. Shay
*Attorney, Agent, or Firm*—Lahive & Cockfield

[57] ABSTRACT

A multi-wavelength surgical laser apparatus of improved construction employs a fluid-filled stimulated Raman scattering cell in an optical feedback path of a pump laser having a power in a range suitable for surgery, and drives the Raman cell at a high repetition rate in a manner to produce a laser output at a substantially shifted wavelength at a power commensurate with that of the pump laser. In a preferred system, the relative proportions of pump light and Raman scattered light are varied to achieve a desired cutting or coagulating action. Preferably, the pump laser is operated at a pulse repetition rate above five hundred Hz. The fluid Raman medium is pumped across the optical axis of the cell. The flow system effectively doubles the Raman conversion efficiency and permits high power output while lowering the Raman lasing threshold. Systems include a fiber for conducting output light to a surgical probe, and a variable output coupler to vary the relative amounts of pump and Stokes radiation coupled into the fiber. Light generated at visible wavelengths by Stokes processes in the Raman cell provides auxiliary beam for targeting or observation purposes.

8 Claims, 2 Drawing Sheets

LASER SURGERY SYSTEM

This is a continuation of application Ser. No. 342,481, filed Apr. 24, 1989, now abandoned.

BACKGROUND OF THE INVENTION

The present invention relates to surgical apparatus for the localized treatment of tissue by the application of light energy, and particularly to the area of laser surgery wherein tissue is cut, cauterized or otherwise subjected to laser light.

In such system there is a complicated set of design constraints imposed, on the one hand, by the available systems for generating laser light at particular wavelengths and powers suitable for different surgical applications, and, on the other hand, by the characteristics of probes or instruments for delivering the light to a surgical site and applying it to cut, coagulate or otherwise treat or analyze tissue.

In broad terms, the efficiency with which light of a given wavelength is absorbed by a particular tissue determines its depth of penetration, and thus the degree to which a pulse of such light will primarily cause either a superficial cutting action and tissue ablation without heat transfer to underlying tissue, or will cause a heating action to a depth effective to cauterize tissue. Both of these actions are generally desired for surgical purposes, thus requiring light of two substantially different wavelengths, at relatively high average power levels. In addition, light of different wavelength at lower powers may also be desirable for visualization or certain forms of analysis, particularly in surgical arenas where the light is applied by endoscopic instrument.

The probes or instruments for delivering such light to a tissue site must guide the light with minimal losses from the laser source, and minimal parasitic heat generation. Two basic structures have evolved to achieve this purpose. In one, a highly reflective metallic tube structure, fabricated as an articulated arm, guides light by internal reflection to a probe end which is aimed at the tissue. In the other, fiber optics serve as the light guide, allowing greater flexibility in the delivery of light to, and manipulation of, the surgical probe. Hybrid delivery systems are also possible, although for particular wavelength bands absorption by the fiber may preclude the use of the fiber optic approach.

These constraints have meant, in practice, that a multi-wavelength surgical apparatus requires several distinct laser light sources, with precision alignment and coupling of the different sources into a common waveguide or probe structure, and the provision of a number of different controls to select working wavelength and set the desired power. These factors affect the production cost, the field reliability and the ease of use of such systems.

SUMMARY OF THE INVENTION

Accordingly, it is an object of the present invention to provide a multi-wavelength surgical laser apparatus of improved construction.

This is accomplished according to a principal aspect of the invention by providing a fluid-filled stimulated Raman scattering cell in an optical feedback path of a pump laser having an output power in a range suitable for surgery, and driving the Raman cell in a manner to produce a laser output at a substantially shifted wavelength at a power commensurate with that of the pump laser. The relative proportion of pump and Raman scattered light are varied to achieve a desired cutting or coagulating action. In a preferred embodiment, the pump laser is operated at a pulse repetition rate between 200 and 3000 Hz, and means are provided to effect flow of the fluid medium across the optical axis of the Raman cell, effectively eliminating thermal lensing effects from the relaxation of stimulated molecules and achieving high Raman conversion efficiency. Lenses at the end of cell concentrate the pump laser output in a narrowed region of high intensity midway along the cell. With this driving arrangement the threshhold power to achieve Raman lasing is substantially lowered and a common Nd:YAG laser may drive the system with high efficiency at average power levels in the range of approximately one to thirty watts.

A prototype system includes a laser source with a hydrogen-filled Raman cell operated at 5–30 atmospheres, which was driven at a pulse rate of up to two kHz by a ten watt Nd:YAG laser at 1.06 microns, to produce an output at approximately 35 percent of the drive photons at 1.9 microns. Systems employing such a laser include a fiber for conducting output light to a surgical probe, and preferably include means for selectively varying the relative amount of pump and Stokes radiation coupled into the fiber. Light generated at visible wavelengths by anti-Stokes processes in the Raman cell provides auxiliary beams for targeting or observation purposes.

BRIEF DESCRIPTION OF THE DRAWINGS

These and other features of the invention will be understood from the following disclosure, the teachings of which will be read in light of the background technology as understood by a person of ordinary skill in the art, and the illustrations of representative embodiments, wherein.

DETAILED DESCRIPTION OF THE INVENTION

Figure 1:
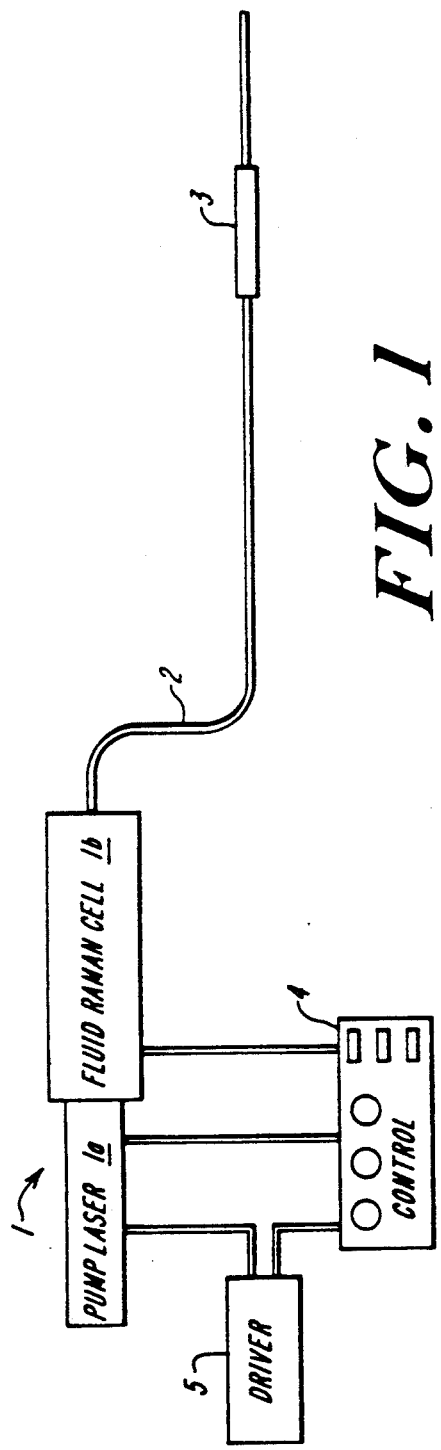
FIG. 1 shows a surgical laser system according to the present invention.

A surgical system according to the invention has a laser source 1 including a pump laser 1a and a fluid Raman lasing cell 1b which operates to produce a relatively high average power laser beam at two or more substantially different wavelengths for surgery Laser 1 is connected by a fiber light guide 2 to a surgical probe 3 which is illustrated schematically probe 3 may be a hand-held laser scalpel for external use, or may be a more complicated device for use in blood vessels or body passages or cavities, wherein the light from fiber 2 is guided to the tip of the probe, and the probe further contains various endoscopic, tip steering, beam forming or material removal or aspirating means or tissue analysis devices. The elements of a probe are considered conventional, and are not described further herein. A controller 4 selects the power, duration and wavelength of light supplied by source 1 to the probe, and a driver module 5 operates the pump laser in a manner to drive the Raman cell at a high average power level.

Figure 2:
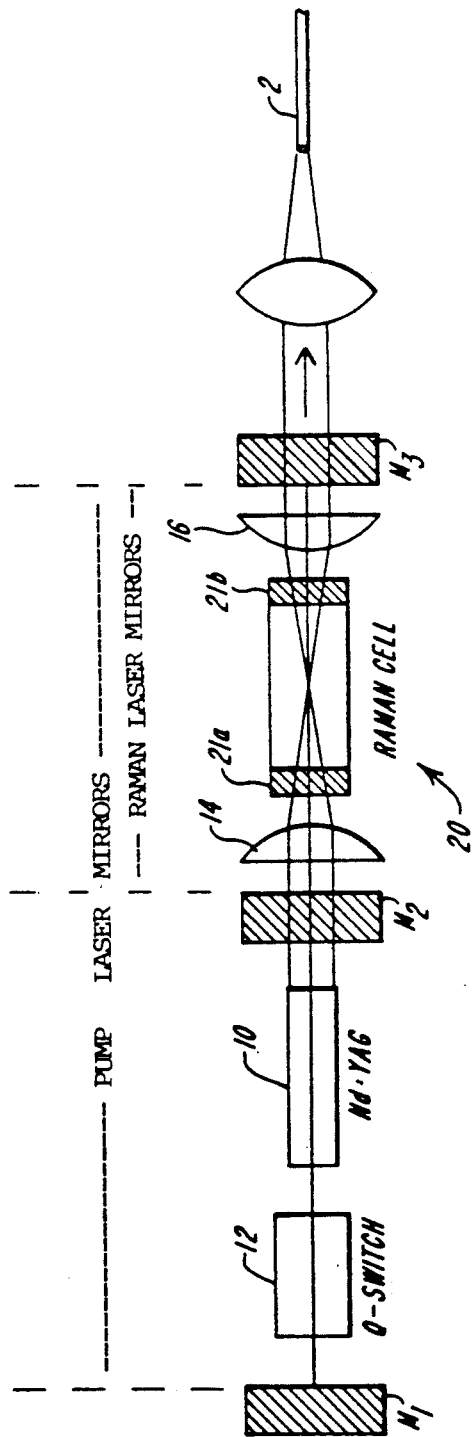
FIG. 2 shows the construction of a preferred embodiment of a surgical laser source according to the invention.

FIG. 2 shows in more detail the construction employed in one prototype of the laser source. In this embodiment, pump laser 1a was a solid state Nd:YAG laser which although subject to power drop-off in the preferred driving arrangement described below was operated to produce an average power output of 4-6 watts at a wavelength of 1.06 microns. The Raman cell was a gaseous hydrogen Raman cell which was arranged in a direct feedback path with the pump laser, and was excited by pulsed 1.06 micron light from the pump laser to emit stimulated Raman scattered light at 1.9 microns. The driving and control system, discussed further below, pumped the cell to produce a light output at a power level comparable to that of the pump laser.

It has long been known that certain gaseous materials, such as deuterium, hydrogen, carbon dioxide and others can undergo stimulation of their internal energy modes by laser light to emit coherent light of a shifted frequency. A dual wavelength source consisting of a Raman cell driven by a pump laser source has previously been proposed as a way of producing a wavelength output shifted from that of a fixed source. Research has shown, however, that the peak power intensity threshhold required for a pump laser to initiate Raman lasing (SRS) emission even in a relatively active Raman scattering material such as hydrogen is in the tens or hundreds of thousands of kilowatts. The lowest threshholds have been demonstrated in special cases, e.g., for the principal $TEM_{oo}$ mode using specialized wave guiding apparatus to achieve the greatest conversion efficiency. For multimode beams the threshholds are higher, and this has effectively ruled out the possibility of achieving a surgically useful level of output from a fluid Raman cell driven by any of the common solid state pump lasers, such as YAG lasers which operate at an average power level of under 100 watts.

Applicant has now overcome these limitations and achieved a sustained output from a gas-filled Raman cell at an average power level suitable for surgery using an inexpensive and relatively small Nd:YAG laser of approximately fifteen watts average power. The fluid-filled Raman cell is made to achieve an effective power output by switching the pump laser at a high repetition rate and focusing light along a feedback path of the pump laser into an interaction region within the Raman cell while a flow of fluid is provided across the interaction region. The lasing threshold is lowered while the Stokes efficiency is raised to a level such that a watt or more of Stokes power is readily generated with the low power pump laser. Such Raman efficiency has previously been possible with pump lasers having an output intensity one or two orders of magnitude higher.

In the prototype experimental arrangement shown in FIG. 2, the pump laser 1a includes a Nd:YAG rod 10 six millimeters diameter by ten centimeters long which is pumped by a single Krypton flashlamp (not shown). An acousto-optic Q-switch 12 is controlled by the driver 5 (FIG. 1) to pulse the laser at repetition rates of up to several kilohertz. The Raman cell 20 is placed in a direct feedback path of the pump laser by an optical design shown as an intracavity three mirror dual laser cavity configuration.

Two mirrors, $M_1$ and $M_3$, form an oscillator cavity for the Nd:YAG pump radiation. These mirrors have a high reflectivity ($R_p > 99.9\%$) dielectric coating at the 1.06 micron pump wavelength. A third, intermediate mirror $M_2$ is placed such that mirrors $M_2$ and $M_3$ confine the Stokes radiation at 1.9 microns of the Raman cell 20. Windows 21a, 21b close the cell. The windows are transmissive at all relevant wavelengths, and serve to contain the high pressure Raman fluid medium. The intracavity mirror, $M_2$, is coated for high transmittance at 1.06 microns ($R_p < 0.5\%$) and high reflectivity at 1.9 microns ($R_s > 99\%$). Mirror $M_3$ is used to output couple the Stokes radiation, and in different embodiments its reflectivity at 1.9 microns is varied, with different optical coatings, to achieve a desired percentage transmittance of that wavelength. Two identical intracavity lenses 14, 16 are placed at the ends of the Raman cell 20, and serve to focus the light in the cavity into a relatively small region at the center of the cell. The intracavity lenses have a focal length of ten centimeters, an f-number of approximately f10-f30, and are placed in a nearly concentric configuration, thus focusing all radiation passing between the mirrors $M_2$ and $M_3$ into a small (under approximately one centimeter long) segment at the center of the Raman cell. Both the intracavity lenses 14, 16 and Raman cell windows 21a, 21b are antireflection coated to achieve less than 0.25% reflectivity per surface at both 1.06 and 1.9 microns wavelengths. Finally, a closed loop flowing gas system circulates hydrogen at 5-20 atmospheres through the cell 20 across the optical axis at linear flow velocities of about 200 cm/sec. The total cavity length is about one meter.

Using the above laser source configuration, the energy per 150 ns pulse of the Nd:YAG laser at a repetition frequency of 1 kHz Was determined and the Raman cell was then filled with hydrogen. Using a Molectron P5-01 fast pyroelectric detector and a Tektronix 7904 500 Mhz oscilloscope, the temporal pulse shapes of the pump and the Stokes radiation were recorded. The beam quality was evaluated for both the pump and the Stokes beams by measuring the spot size focused from the beam by an extracavity lens, and comparing it to the size of a theoretically calculated diffraction-limited beam of the same aperture. Finally, the average output Stokes power was measured as a function of repetition rate for both a static and a flowing fluid in the cell.

A detailed consideration of theoretical models as well as measurements on pump laser and stimulated Raman emissions was undertaken for the experimental system shown in FIG. 2, with different mirrors $M_3$ substituted. The mirror $M_3$ was highly reflective at the pump wavelength, and was coated to provide a preselected reflectance $R_s$ at the Stokes wavelength between 3% and 90% (Rs = 10%, 64% or 97%). It thus served as a selected ratio output coupler for the Stokes wavelength beam. It will be understood that other arrangements can be provided in the light feedback loop to variably couple different proportions of the pump and the Raman beams out of the laser into the fiber 2 (FIG. 1).

Using such a configuration to explore Stokes conversion efficiencies at a repetition rate of 100 Hz with a 150 ns pump pulse, applicant observed a shorter, approximately 100 ns, Stokes pulse, with a peak conversion efficiency occurring when mirror $M_3$ coupled approximately 30-40% of the Stokes energy as the output. Elementary observations on pump and Stokes beam quality also revealed that the Raman cell was operating to clean up the laser beam, by forming a Stokes beam of better quality than the pump beam. The result was a Stokes beam capable of better focusing, thus enhancing its usefulness for fiber optic applications. Measurements on the beams indicated that while the multimode pump laser beam had under approximately twenty percent of its power in the TEM$_{oo}$ mode, the Stokes output beam had over ninety percent of its power in the TEM$_{oo}$ mode. Further, the TEM$_{oo}$ absolute power level in the Stokes beam exceeded that in the pump beam.

Figure 3:
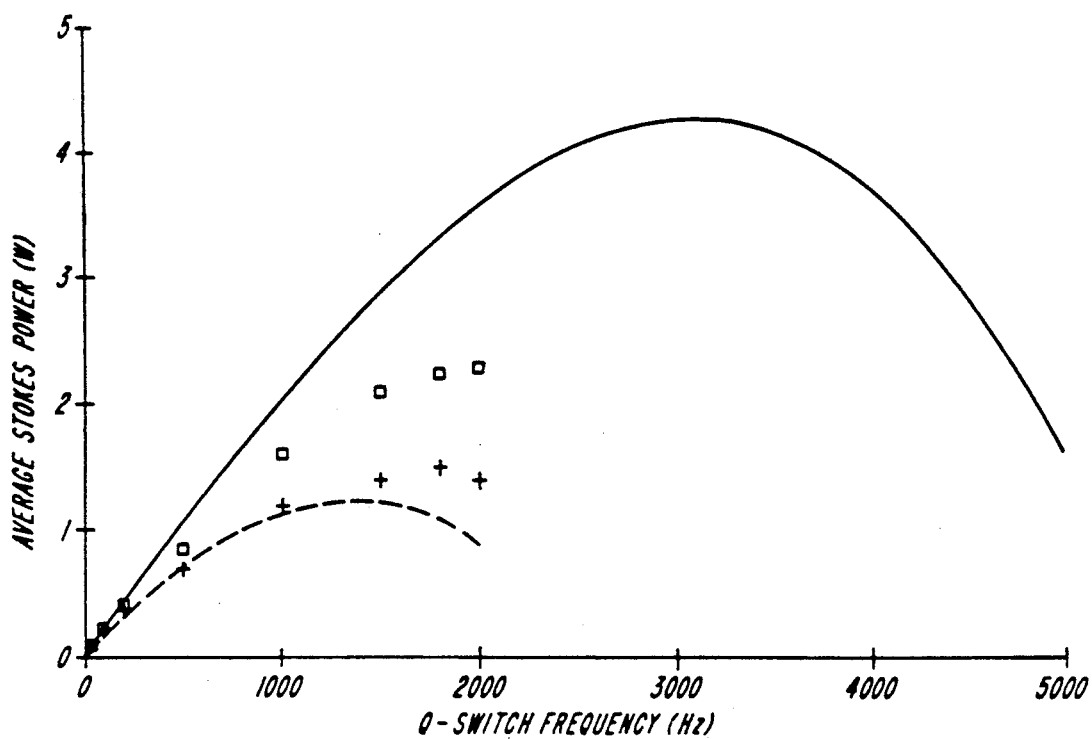
FIG. 3 is a graph showing measured Stokes power as a function of pump laser pulse frequency for a static and a cross-flow Raman cell.

As the pulse repetition rate was increased the total average power increasingly departed from being linear in repetition rate. The dashed line in FIG. 3 represents a computer-modeled calculation of Stokes output power with frequency, without any flow of gas through the Raman cell. The Raman-active central region of the cell is subject to extreme thermal gradients. The resulting variation of refractive index disrupts the focusing of light into the center of the cell and causes the significant drop in efficiency. The effects of this thermally-induced beam scattering or "thermal lensing" are modeled in the dashed-line graph. FIG. 3 also shows the computer-modeled Stokes laser power (solid line) in watts, as a function of the Q-switching rate. The power drop-off at Q-switching frequencies of the pump laser above 2000 Hz is primarily due to the 0.25 millisecond fluorescence lifetime of the Nd:YAG crystal at the 10.6 micron pump frequency, and the consequent lowering of inversion population at higher frequencies.

The experimental data points indicated by crosses were measured for a Raman cell filled with a stationary medium, and they closely fit the modeled Raman drop-off data, rising only to about one and a half watts at two kilohertz. Finally, the experimental data points indicated by square boxes were measured when a flow of the Raman fluid through the cell was maintained to remove from the optical path a portion of that fluid which had been excited by the previous pump pulse. The Stokes output remained linear well above the modest 300 Hz rate at which the stationary fluid cell degraded. While a drop in per-pulse efficiency above one kHz was noted, as compared with the computed curve (solid line) this is attributed to the limited flow rate achieved by the experimental flow mechanism, as described below.

Figure 4:
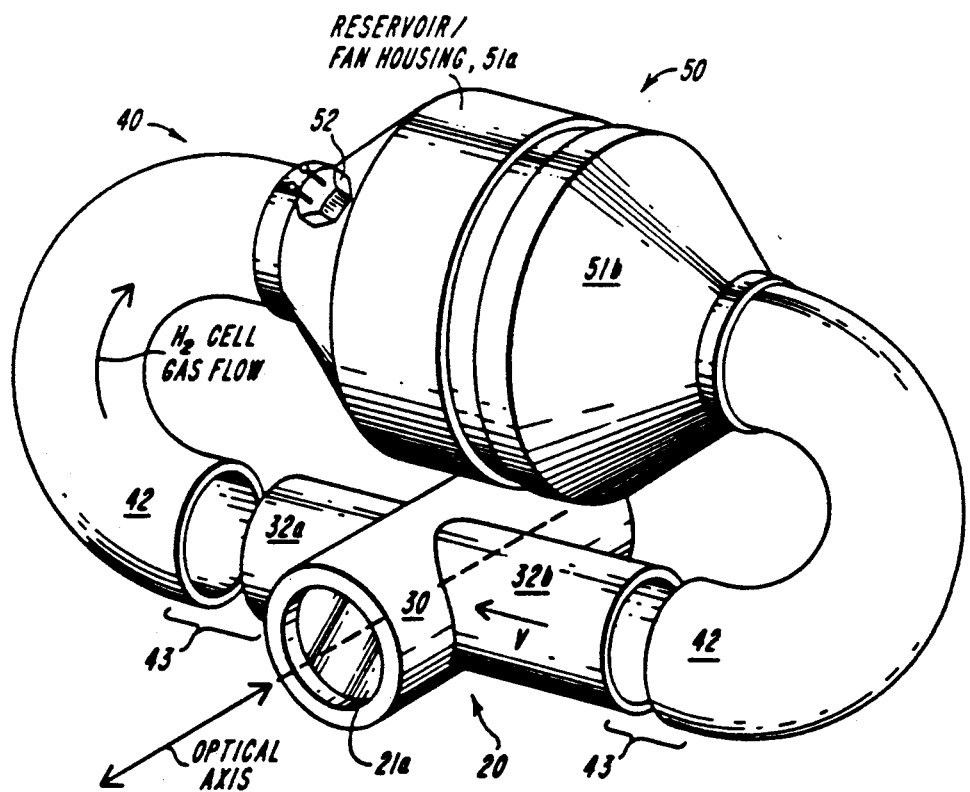
FIG. 4 shows the construction of a cross-flow Raman cell used in the embodiment of FIG. 2.

FIG. 4 shows the overall construction of the cross-flow Raman cell 20 used in the above experiments. The cell 20 was filled with gaseous hydrogen maintained at a pressure between ten and twenty atmospheres, and was part of a Closed fluid circulation system 40 having as basic element a reservoir/fan housing 50, the Raman cell 20, and connecting conduits 42 all connected in a fluid flow loop.

Reservoir/fan housing 50 is formed of two fluid-sealable separable half drums 51a, 51b, with an electrical feed-through 52 for an electric circulating fan (not shown) located in half drum 51a. Preferably vanes or baffles are provided in the flow path through the reservoir to enhance contact of the circulating gas with the housing and promote thermal conduction from the gas. In this aspect, the housing serves to dissipate heat from the circulating gas to the external environment.

The body of the Raman cell 20 is formed as a cross of 2.5 centimeter OD stainless steel conduit, with an axially oriented tubular member 30 having its ends closed by windows 21a, 21b instituting the lasing cell as shown in FIG. 2, and transversely oriented conduit branches 32a, 32b joined at the center of the cell. The conduits 42 are welded to the cross conduits at 43, closing the circulation loop, and a slidable O-ring seal structure is provided at the junction of a conduit 42 with housing 51b to allow disassembly of the housing. Various flange couplings, seals and packing arrangements may be used at any of the junctions, and are not specifically illustrated. One or more valved filler ports may be provided, preferably in the housing 50, for evacuating and filling the system. The fluid circulating fan is selected to provide a flow rate of approximately 500 cc/sec., thus providing a gas cross-flow at a speed in excess of 150 cm./sec at the focal region in the center of cell 20.

Applicant found that when the above described system was operated at a fluid pressure of approximately ten atmospheres, the system produced a significant amount of CARS radiation at 0.737 and 0.534 microns, suitable for laser targeting and tissue observation.

In the prototype system, the focal region of the cell provided an interaction region of approximately one millimeter diameter or less in which active Raman laser processes occurred. The above flow rates were effective to fully replace the medium directly in the excitation path at pump laser repetition rates up to about one kilohertz, but as the repetition rate was raised beyond that frequency, the thermal diffusion rate of the gaseous hydrogen allowed an increasingly significant amount of gas to reside in the interaction area. This previously-stimulated gas, which was not in its ground vibrational state, accounted for the drop-off from linearity in measured energy noted in FIG. 3. In further embodiments, the cross flow circulation system is preferably of a capacity to provide a cross-flow of gas between pulses which is greater than the interaction width by an amount greater than the characteristic interpulse thermal diffusion distance of the gaseous medium. For the above described optical configuration and cell dimensions, a cross-flow velocity of 500–1000 cm./sec. should be adequate for repetition rates up to three kiloherz.

As described above, the invention achieves a substantially shifted wavelength from that of a solid state pump laser in a fluid Raman scattering cell at a power commensurate with that of the pump laser. The substantially lowered Raman lasing threshhold allows for the first time the practical application of large Raman shifts to a class of low power solid state lasers, and the provision of surgically effective power levels into fiber-compatible delivery systems.

While the output coupling of the two laser colors into the fiber has been described in terms of the use of partially reflective mirrors, other output coupling schemes, including polarization control, and filtering of the output light, may be employed in the described laser source to vary the light of each wavelength which is coupled into the fiber 2. One such means is the substitution for mirror M$_3$ of a piezo-electrically controlled interference filter, such as a Fabry-perot interferometer, as an output coupler with variable reflectivity at the pump wavelength. Such variable reflectivity is achievable by varying the gap between two optical flats each having proper reflectivity coatings at the pump wavelength. The reflectivity for the Stokes wavelength is maintained at an optimal value. By varying the gap of the Fabry-perot interferometer, the output is then made to vary from mostly Stokes to mostly pump outputs. With high output coupling at the pump wavelength, no Stokes beam will be generated, while low output coupling at the pump wavelength will yield mostly Stokes output.

It will be understood that while the prototype embodiment was implemented with a Nd:YAG pump laser and gaseous hydrogen Raman cell to produce laser power at 1.06 microns and 1.9 microns adapted to fiber optic transmission and wavelengths having different surgical properties, other pump and Raman lasers are contemplated to achieve different operative wavelengths in systems according to the invention. In other embodiments, the teachings of the invention may be advantageously applied to other Raman-active media, including $D_2$, $N_2O$, $CO_2$, $SF_6$, NO, CO, HBr, $N_2$ and others.

The invention being thus disclosed and described in connection with the illustrated embodiments, variations and modifications thereof will occur to those skilled in the art, and are intended to be included within the scope of the invention, as defined by the claims appended hereto.

What is claimed is:

1. A medical laser source for the generation of laser light suitable for fiber optic delivery at a power level effective for performing surgery, such medical laser source comprising a solid state pump laser providing a pulsed multimode beam at a first wavelength $\lambda_o$ and having a $TEM_{oo}$ mode as a minor component a gas filled Raman cell driven by said multimode beam arranged in an optical feedback path with said pump laser for producing a Stokes beam at a shifted wavelength $\lambda_1$ in said Raman cell cross flow means for providing a flow of gas across a central region of said Raman cell optical means for focusing the pulsed multimode beam into said central region output coupling means for coupling light from said Raman cell to an optical fiber said optical means focusing the multimode beam into said central region with an intensity effective to produce said Stokes beam with a $TEM_{oo}$ mode as a primary component, and said cross flow means being operable to provide a flow across said central region to overcome thermal lensing when said pump laser is pulsed at a repetition rate in excess of approximately 100 Hz, whereby said laser source efficiently wavelength shifts and cleans up the multimode beam of the pump laser to produce a substantially single mode beam for fiber optic delivery while achieving an effective power level for surgery.

2. A medical laser source according to claim 1, wherein the pump laser applies pulses into a region of said Raman cell at a pulse repetition rate over 300 $sec^{-1}$ while the cross flow means provides a cross flow within the cell at a rate sufficient to maintain Raman scattering efficiency in the central region.

3. A medical laser source according to claim 1, wherein the flow is provided at a rate such that between consecutive pulses of the pump laser the gas in the central region is displaced further than a transverse diameter of the central region plus a characteristic diffusion distance of the gas.

4. A medical laser source according to claim 1, further including output control means for varying amounts of light at wavelengths $\lambda_0$ and $\lambda_1$ coupled as an output from the Raman cell.

5. A medical laser source according to claim 1 wherein said solid state pump laser is a Nd laser and said Raman cell is a hydrogen cell, producing $\lambda_1$ and $\lambda_1$ of 1.06 microns and 1.9 microns, respectively.

6. A medical laser source according to claim 1, wherein the substantially beam has greater absolute power in the $TEM_{oo}$ mode than has the pump laser.

7. A medical laser source according to claim 1, wherein said pump laser is a Q-switched YAG laser.

8. A medical laser source according to claim 7, wherein said Raman cell is a hydrogen-filled Raman cell operated to produce a visible CARS beam for targeting or observation of a surgical probe.

* * * * *

UNITED STATES PATENT AND TRADEMARK OFFICE
CERTIFICATE OF CORRECTION

PATENT NO. : 5,180,378

DATED : January 19, 1993

INVENTOR(S) : Robert T. Kung and Robert B. Stewart

It is certified that error appears in the above-identified patent and that said Letters Patent is hereby corrected as shown below:

On the title page, in the assignee data section labeled [73], replace "Danivers, Massachusetts" with --Danvers, Massachusetts--.

On the title page, in line 21 of the text of the Abstract, replace "auxiliary beam" with --auxiliary beams--.

Column 1, line 50, after "light sources," replace "With" by --with--.

Column 2, line 56, after "surgery" insert --.--.

Column 2, line 58, replace "schematically probe" with --schematically. Probe--.

Column 4, line 32, replace "Was" with --was--.

Column 5, line 23, replace "10.6 micron" with --1.06 micron--.

Column 6, line 52, replace "Fabry-perot" with --Fabry-Perot--.

Column 6, lines 59, replace "Fabry-perot" with --Fabry-Perot--.

UNITED STATES PATENT AND TRADEMARK OFFICE
CERTIFICATE OF CORRECTION

PATENT NO. : 5,180,378

DATED : January 19, 1993

INVENTOR(S) : Robert T. Kung and Robert B. Stewart

It is certified that error appears in the above-identified patent and that said Letters Patent is hereby corrected as shown below:

*In the Claims*

Claim 1, column 7, line 23, after "cell driven", insert --only--.

Claim 5, column 8, line 27, replace "producing $\lambda_1$ and $\lambda_1$" with --producing $\lambda_0$ and $\lambda_1$--.

Claim 6, column 8, line 30, replace "the substantially beam" with --the output beam--.

Signed and Sealed this

Seventeenth Day of May, 1994

*Attest:*

BRUCE LEHMAN

*Attesting Officer*  *Commissioner of Patents and Trademarks*